(12) United States Patent
Harrison et al.

(10) Patent No.: US 10,119,139 B2
(45) Date of Patent: Nov. 6, 2018

(54) TREATMENT FOR CONDITIONS ASSOCIATED WITH FIBROSIS AND COLLAGEN DEPOSITION

(71) Applicants: Vanderbilt University, Nashville, TN (US); Yale University, New Haven, CT (US)

(72) Inventors: David G. Harrison, Nashville, TN (US); Kim Ramil Montaniel, Antioch, TN (US); Kasey C. Vickers, Franklin, TN (US); Jing Wu, Lexington, KY (US); Jay D. Humphrey, Madison, CT (US); Matthew R. Bersi, Nashville, TN (US)

(73) Assignees: Vanderbilt University, Nashville, TN (US); Yale University, New Haven, CT (US)

( * ) Notice: Subject to any disclaimer, the term of this patent is extended or adjusted under 35 U.S.C. 154(b) by 0 days.

(21) Appl. No.: 15/265,813

(22) Filed: Sep. 14, 2016

(65) Prior Publication Data

US 2017/0073676 A1    Mar. 16, 2017

Related U.S. Application Data

(60) Provisional application No. 62/218,405, filed on Sep. 14, 2015.

(51) Int. Cl.

| | |
|---|---|
| *C12N 15/113* | (2010.01) |
| *A61K 45/06* | (2006.01) |
| *A61K 31/7105* | (2006.01) |
| *C12Q 1/6883* | (2018.01) |
| *A61B 17/22* | (2006.01) |

(52) U.S. Cl.
CPC ........ *C12N 15/113* (2013.01); *A61K 31/7105* (2013.01); *A61K 45/06* (2013.01); *C12Q 1/6883* (2013.01); *A61B 17/22* (2013.01); *A61B 2017/22001* (2013.01); *A61B 2017/22051* (2013.01); *C12N 2310/113* (2013.01); *C12N 2310/322* (2013.01); *C12N 2310/3231* (2013.01); *C12N 2320/31* (2013.01); *C12Q 2600/158* (2013.01); *C12Q 2600/178* (2013.01)

(58) Field of Classification Search
CPC ..................................................... A61K 48/00
See application file for complete search history.

(56) References Cited

U.S. PATENT DOCUMENTS

| | | |
|---|---|---|
| 2012/0165392 A1 | 6/2012 | Olson et al. |
| 2013/0005658 A1 | 1/2013 | Olson et al. |
| 2013/0216605 A1 | 8/2013 | Mohapatra et al. |
| 2016/0251656 A1* | 9/2016 | Berriel Diaz ........ C12N 15/113 |

OTHER PUBLICATIONS

Lan et al. (Cardiovascular Pathology 22 (2013): 401-407).*
Gui, et al., MicroRNAs that target Ca2 þ transporters are involved in vascular smooth muscle cell calcification, Laboratory Investigation | vol. 92 Sep. 2012, pp. 1250-1259.
Tsoa, et al., Cross-Sectional Relations of Arterial Stiffness, Pressure Pulsatility, Wave Reflection, and Arterial Calcification, Arterioscler Thromb Vasc Biol, Nov. 2014, pp. 2495-2500.

* cited by examiner

*Primary Examiner* — Kimberly Chong
(74) *Attorney, Agent, or Firm* — Stites & Harbison PLLC; Mandy Wilson Decker; Sean P. Ritchie

(57) ABSTRACT

Methods, compositions, devices, and kits for treating and/or reducing the risk of developing a condition associated with fibrosis and/or collagen deposition are provided. The method of treating and/or reducing the risk of developing a condition associated with fibrosis and/or collagen deposition in a subject includes administering an effective amount a miRNA-762 inhibitor to the subject, wherein the subject is identified as having a risk of developing and/or a need for treatment of the condition associated with fibrosis and/or collagen deposition. The kit includes a vial containing an miRNA-762 inhibitor and a device for use in a surgery creating a risk of fibrosis and/or collagen deposition. The composition includes a pharmaceutical composition comprising a miRNA-762 inhibitor and a second agent selected from the group consisting of: an angiotensin-converting enzyme (ACE) inhibitors, an angiotensin receptor blocker (ARB), another antihypertensive agent, a steroid, and combinations thereof.

17 Claims, 10 Drawing Sheets

Specification includes a Sequence Listing.

* Indicates energy at systolic pressure

SEQUENCE LISTING

```
<160> NUMBER OF SEQ ID NOS: 2

<210> SEQ ID NO 1
<211> LENGTH: 22
<212> TYPE: RNA
<213> ORGANISM: Artificial
<220> FEATURE:
<223> OTHER INFORMATION: Mus musculus miR-762

<400> SEQUENCE: 1
ggggcugggg ccgggacaga gc                                              22

<210> SEQ ID NO 2
<211> LENGTH: 16
<212> TYPE: DNA
<213> ORGANISM: Artificial
<220> FEATURE:
<223> OTHER INFORMATION: antagomiR-762

<400> SEQUENCE: 2
ctctgtcccg gcccca                                                     16
```

TREATMENT FOR CONDITIONS ASSOCIATED WITH FIBROSIS AND COLLAGEN DEPOSITION

RELATED APPLICATIONS

This application claims priority from U.S. Provisional Application Ser. No. 62/218,405, filed Sep. 14, 2015, the entire disclosure of which is incorporated herein by this reference.

GOVERNMENT SUPPORT

This invention was made with government support under HL390006, HL058000, and HL105294 awarded by the National Institutes of Health. The government has certain rights in the invention.

TECHNICAL FIELD

The presently-disclosed subject matter relates to treating and reducing risk of conditions associated with fibrosis and collagen deposition. In particular, the presently-disclosed subject matter relates to inhibiting mircoRNA-762 to treat and reduce risk of such conditions.

BACKGROUND

Fibrosis is characterized by excessive matrix deposition in a tissue or an organ during a reactive or reparative process. It is a major public health burden being implicated in nearly 45% of natural deaths in the western world. Fibrosis is observed in multiple disease including kidney disease, idiopathic pulmonary fibrosis (IPF), scleroderma, and cardiovascular disease.

For example, fibrosis has specifically been observed in hypertension, which is characterized by systolic and diastolic blood pressure greater than about 130 and 80 mmHg, respectively. Normally, the capacitance property of the aorta blunts blood pressure elevation during systole and maintains diastolic pressure and tissue perfusion during diastole. However, the present inventors recently showed that hypertension causes a striking deposition of collagen in the aortic adventitia. This deposition of collagen is associated with marked alteration in aortic compliance indicative of increased stiffness. In vivo, this increase in aortic stiffness leads to a loss of Windkessel or capacitance function of the aorta, increasing systolic pressure and pulse wave velocity, decreasing diastolic pressure, and promoting hypertension-related end-organ damage. In particular, the augmentation of systolic pressure caused by aortic stiffening may increase the incidence of stroke, renal failure, and myocardial infarction.

As such, hypertension is a major risk factor for cardiovascular mortality and morbidity, predisposing to myocardial infarction, stroke and heart failure. In western societies, hypertension affects approximately 30% of adults and by age 70, 70% of individuals are hypertensive. Not only is hypertension highly prevalent, treatment thereof generally requires multiple agents and is often unsuccessful.

That said, it has recently become apparent that microRNAs (miRNAs) contribute to pathophysiology of numerous diseases. MicroRNAs (miRNAs) are short non-coding RNAs, which are present in plants, animals and some viruses. MicroRNAs are synthesized as pri-miRNA that contain a hairpin loop. The enzyme dicer removes the hairpin loop leaving a double stranded miRNA duplex. One strand joins a group of proteins called the argonaute complex while the other strand called the "passenger strand" is usually discarded. The argonaute-attached miRNA (now called the RNA induced silencing complex or RISC) then binds its target mRNAs and either enhances mRNA degradation or blocks translation. miRNAs often bind to mRNAs that encode proteins in common pathways, and can thus serve as regulators of important physiological processes.

Currently, little is known about the role of miRNAs in hypertension. For example, although it has been suggested that miR-145 is prevalent in vascular smooth muscle cells and that it regulates blood pressure, preliminary data of the present inventors have failed to confirm this. Another miRNA potentially related to hypertension is miR-155, which targets the angiotensin II receptor type I (AT1R). Overexpression of this blunts angiotensin II signaling in primary lung fibroblasts. miR-155 is prevalent in atherosclerotic plaques and in pro-inflammatory macrophages and its absence reduces atherosclerotic lesion formation in ApoE−/−mice. Thus, there remain very few, if any, treatment strategies available that specifically target the pathogenesis of fibrosis and/or collagen deposition associated with hypertension.

Accordingly, there remains a need in the art for treatment of conditions associated with fibrosis and/or collagen deposition, such as, for example, treatment of aortic stiffening

SUMMARY

The presently-disclosed subject matter meets some or all of the above-identified needs, as will become evident to those of ordinary skill in the art after a study of information provided in this document.

This summary describes several embodiments of the presently-disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this summary or not. To avoid excessive repetition, this Summary does not list or suggest all possible combinations of such features.

In some embodiments of the presently-disclosed subject matter includes a method of treating and/or reducing the risk of developing a condition associated with fibrosis and/or collagen deposition in a subject, comprising administering an effective amount of a miRNA-762 inhibitor to the subject, wherein the subject is identified as having a risk of developing and/or a need for treatment of the condition associated with fibrosis and/or collagen deposition. In one embodiment, the method also includes determining the levels of miR-762 in a sample from the subject. In another embodiment, the sample includes excess levels of miR-762 as compared to a control.

In certain embodiments, the condition is selected from the group consisting of: aortic stiffening/hypertension, vascular fibrosis, vascular disease, cardiovascular disease, interstitial pulmonary fibrosis, diastolic dysfunction, heart failure with preserved ejection fraction, renal fibrosis, pulmonary fibrosis, kidney fibrosis, lung fibrosis, atherosclerosis, fibrotic diseases/tissue fibrosis, systemic sclerosis, restenosis associated with vascular surgery (including but not limited to stenting or angioplasty), keloid formation, hypertrophic scars, fibromuscular dysplasia, systemic scleroderma, excessive scarring after surgery, myocardial fibrosis, esophageal stricture, joint contracture after immobilization, vascular inflammation, renal inflammation, cerebral inflammation, and Dupuytren's contracture.

In some embodiments, the miRNA-762 inhibitor is an oligonucleotide of 8-49 nucleotides in length having a sequence targeted to miRNA-762, or a precursor thereof. For example, in one embodiment, the oligonucleotide is an antisense oligonucleotide that is at least partially complementary to the sequence of the target miRNA, or a precursor thereof. In another embodiment, the antisense oligonucleotide is selected from the group consisting of a ribonucleotide, a deoxyribonucleotide, an anti-sense molecule, a siRNA molecule, a shRNA molecule, a miRNA sponge, a cDNA, an antagomir, a locked nucleic acid (LNA) oligonucleotide, a decoy oligonucleotide, a peptide nucleic acid (PNA), a morpholino oligonucleotide, or a combination thereof. In a further embodiment, the LNA oligonucleotide is selected from the group consisting of a nucleotide sequence comprising at least 16 contiguous nucleotides complementary to the nucleotides of SEQ ID NO: 1 and the sequence of SEQ ID NO. 2 and modifications excluding base substitutions thereof, and fragments consisting of subsequences of SEQ ID NO: 2 of at least 8 contiguous nucleotides thereof. Additionally or alternatively, the oligonucleotide may be modified to include a 2'-deoxy-2'-fluoro-beta-D-arabinose backbone.

In some embodiments, the miRNA-762 inhibitor is associated with a carrier molecule. Suitable carrier molecules include, but are not limited to, a nanoparticle, a liposome, and a lipoprotein.

In some embodiments, the miRNA inhibitor is administered following an event creating a risk of fibrosis and/or collagen deposition. In some embodiments, the subject does not have vascular calcification.

The inhibitor may be administered by any suitable route. For example, in some embodiments, the inhibitor is administered at a site of fibrosis, scarring, or keloid. Additionally or alternatively, the inhibitor is administered topically or by local injection.

In some embodiments, the inhibitor is associated with a device. In one embodiment, the device includes an implantable device. In another embodiment, the device is a stent coated with the inhibitor. Other devices may include a bandage comprising the inhibitor.

Also provided in some embodiments is a kit including a vial containing an miRNA-762 inhibitor and a device for use in a surgery creating a risk of fibrosis and/or collagen deposition. In one embodiment, the device is selected from the group consisting of an angioplasty balloon and a stent.

Further provided in some embodiments is a pharmaceutical composition comprising: a miRNA-762 inhibitor and a second agent selected from the group consisting of: an angiotensin-converting enzyme (ACE) inhibitors, an angiotensin receptor blocker (ARB), another antihypertensive agent, a steroid, and combinations thereof. In one embodiment, the another antihypertensive agent is selected from the group consisting of: calcium channel blockers, diuretics, beta-adrenergic or alpha adrenergic blocking agents, sympatholytics, and thiazide diuretics.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are used, and the accompanying drawings of which:

BRIEF DESCRIPTION OF THE SEQUENCE LISTING

GGGGCUGGGGCCGGGACAGAGC  SEQ ID NO: 1

CTCTGTCCCGGCCCCA  SEQ ID NO: 2

Description of Exemplary Embodiments

Figure 1A:
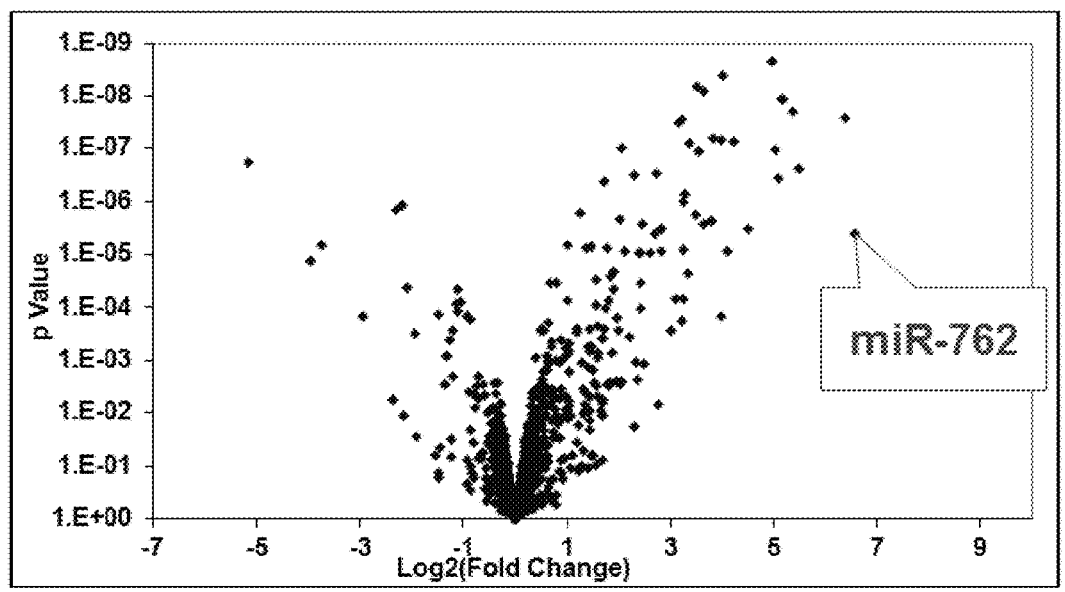
FIG. 1A-B show graphs illustrating the effect of angiotensin II-induced hypertension on vascular miR-762. C57Bl/6 mice received angiotensin II (490 ng/kg/min) or sham for two weeks. Immediately after euthanasia, thoracic aortas were harvested for RNA extraction. cDNA was reverse transcribed and qRT-PCR for miR-762 performed. (A) Volcano plot showing miR-762 as the most highly upregulated miRNA after Ang II infusion. (B) Bar graph confirming that miR-762 is highly upregulated in the aorta after Ang II infusion.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by those of ordinary skill in the art, certain definitions are set forth to facilitate explanation of the presently-disclosed subject matter. Unless defined otherwise, all technical and scientific terms used herein have the same meaning as commonly understood by one of ordinary skill in the art to which the presently-disclosed subject matter belongs.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The term "fibrosis" is well known in the art and is used herein to refer to the formation or development or accumulation of excess fibrous tissue in an organ or tissue as a reparative or reactive process, as opposed to a formation of fibrous tissue as a normal constituent of an organ or tissue.

The term "collagen deposition" and "excessive" or "abnormal" collagen deposition are known in the art. The terms "excessive" or "abnormal collagen deposition" refer to the formation or development or accumulation collagen that is in excess to that which is part of a normal process of inflammation and healing, and which can characterize certain conditions.

In certain instances, microRNAs (miRNAs) disclosed herein are identified with reference to names assigned by the miRBase Registry (available at www.mirbase.org). The sequences and other information regarding the identified miRNAs as set forth in the miRBase Registry are expressly incorporated by reference as are equivalent and related miRNAs present in the miRBase Registry or other public databases. Also expressly incorporated herein by reference are all annotations present in the miRBase Registry associated with the miRNAs disclosed herein. Unless otherwise indicated or apparent, the references to the Sanger miRBase Registry are references to the most recent version of the database as of the filing date of this Application (i.e., mirBase 21, released June 2014).]

Although any methods, devices, and materials similar or equivalent to those described herein can be used in the practice or testing of the presently-disclosed subject matter, representative methods, devices, and materials are now described.

In some embodiments, the presently-disclosed subject matter is directed methods, compositions, devices, and kits for treating and/or reducing the risk of developing a condition associated with fibrosis and/or collagen deposition. Conditions associated with fibrosis and/or collagen deposition include, but are not limited to, aortic stiffening/hypertension, vascular fibrosis, vascular disease, cardiovascular disease, interstitial pulmonary fibrosis, diastolic dysfunction, heart failure with preserved ejection fraction, renal fibrosis, pulmonary fibrosis, kidney fibrosis, lung fibrosis, atherosclerosis, fibrotic diseases/tissue fibrosis, systemic sclerosis, restenosis associated with vascular surgery (including but not limited to stenting or angioplasty), keloid formation, hypertrophic scars, fibromuscular dysplasia, systemic scleroderma, excessive scarring after surgery, myocardial fibrosis, esophageal stricture, joint contracture after immobilization, vascular inflammation, renal inflammation, cerebral inflammation, Dupuytren's contracture, conditions as set forth in Table 1, and combinations thereof.

In some embodiments, the methods, compositions, devices, and kits disclosed herein make use of a miRNA-762 inhibitor. More specifically, in one embodiment, miRNA-762 and miRNA-762 inhibitor are used in connection with conditions associated with fibrosis and/or collagen deposition. As will be recognized by one of ordinary skill in the art, there is a clear distinction between conditions associated with fibrosis and/or collagen deposition, and the previously suggested connection between miRNA-762 and vascular smooth muscle cell (VSMC) calcification, asthma and other inflammatory diseases, and myocardial infarction. See Gui, et al., "MicroRNAs that target $Ca^{2+}$ transporters are involved in vascular smooth muscle cell calcification," Laboratory Investigation (2012) 92, 1250-1259; and U.S. Patent Application Publication Nos. 2013/0216605, 2013/0005658, and 2012/0165392. For example, calcification has a molecular mechanism that does not overlap with that of vascular fibrosis and collagen deposition, and subjects in need of treatment for a condition associated with vascular fibrosis and collagen deposition can be identified by clinical methods known in the art, and can be distinguished from subjects in need of treatment for VSMC calcification. In this regard, Table 1 includes some additional information.

TABLE 1

| Disease | Role of Fibrosis/Collagen deposition | Role of calcium deposition |
|---|---|---|
| Aortic stiffening/ hypertension | Augmented hypertension and damage to peripheral organs | None known |
| Renal fibrosis | Occurs in aging, hypertension, miscellaneous diseases. Leads to renal failure, hypertension | None known |
| Pulmonary fibrosis | Devastating disease leading to severe disability and death caused by fibrosis | None known |
| Atherosclerosis | Fibrosis occurs in plaque and stabilizes the lesion, but can become exuberant and worsen stenosis | Calcium flecks are a marker of the disease. |
| Restenosis associated with stenting or angioplasty | Also referred to as neointimal formation. Matrix/collagen deposition is major cause | Calcium flecks might be present |
| Keloid formation | Common disfiguring scar formation. More common in African-Americans | None known |
| Systemic scleroderma | fibroblast dysfunction collagen accumulation and other matrix components in skin and internal organs | Calcinosis cutis can occur |
| Excessive scarring after surgery | Leads to gastrointestinal adhesions, pericardial constriction, makes repeat surgery difficult/impossible | Calcium might be deposited but is an after-effect |
| Myocardial fibrosis | Could contribute to diastolic dysfunction, a major cause of heart failure | None known |
| Esophageal stricture | Can cause major disability due to inability to swallow | None known |
| Joint contracture after immobilization | Occurs after immobilization. Involves collagen deposition. Adhesions of synovium | None known |
| Dupuytren's contracture | Disfiguring and disabling excessive fibroblast and collagen deposition in tendons. | None known |

As briefly described above, in some embodiments, the presently-disclosed subject matter includes a method of treating and/or reducing the risk of developing a condition associated with fibrosis and/or collagen deposition in a subject. In one embodiment, the method involves administering an effective amount a miRNA-762 inhibitor to the subject, wherein the subject is identified as having a risk of developing and/or a need for treatment of the condition associated with fibrosis and/or collagen deposition. In another embodiment, the method also involves determining the levels of miR-762 in a sample from the subject. In a further embodiment, the sample includes excess levels of miR-762 as compared to a control.

Without wishing to be bound by theory, it is believed that miR-762 is a pro-fibrotic miRNA. Accordingly, in some embodiments, inhibiting the function of miR-762 in vivo inhibits and/or reverses aortic fibrosis and/or stiffening. In certain embodiments, inhibiting the function of miR-762 inhibits and/or reverses aortic fibrosis and/or stiffening despite persistence of hypertension. For example, in one embodiment, the presently-disclosed subject matter contemplates miR-762 inhibition for treatment of conditions associated with fibrosis and/or collagen deposition, such as, for example, treatment of aortic stiffening. Additionally or alternatively, the presently-disclosed subject matter contemplates miR-726 inhibition for treatment of renal inflammation and/or fibrosis.

As used herein, the terms "treatment" or "treating" relate to any treatment of a condition associated with fibrosis and/or collagen deposition including but not limited to prophylactic treatment to prevent development or reduce severity of a disorder, as well as therapeutic treatment. In this regard, in is understood that prophylactic treatment does not refer to a complete prevention of any sign of the condition, but rather to a reduction of risk of developing the condition and/or reducing the severity of the condition. In this regard, it is also understood that therapeutic treatment relate to curing or substantially curing a condition, as well as ameliorating at least one symptom of the condition and/or reducing the severity of the condition.

The term "miRNA inhibitor" refers to an agent or molecule that inactivates or decreases the activity of the miRNA. As will be recognized by one of ordinary skill in the art, the term "inhibiting" or "inhibition" does not refer to the ability to completely inactivate all activity in all cases. Rather, the skilled artisan will understand that the term "inhibiting" refers to decreasing activity of the target. Such decrease in biological activity can be determined, for example, by an assay relative to a control, wherein an inhibitor is not administered and/or placed in contact with the target.

In some embodiments, the miRNA-762 inhibitor is an oligonucleotide of 8-49 nucleotides in length having a sequence targeted to miRNA-762, or a precursor thereof. For example, in one embodiment, the oligonucleotide is an antisense oligonucleotide that is at least partially complementary to the sequence of the target miRNA, or a precursor thereof. In another embodiment, the antisense oligonucleotide includes a ribonucleotide, a deoxyribonucleotide, an anti-sense molecule, a siRNA molecule, a shRNA molecule, a miRNA sponge, a cDNA, an antagomir, a locked nucleic acid (LNA) oligonucleotide, a decoy oligonucleotide, a peptide nucleic acid (PNA), a morpholino oligonucleotide, or a combination thereof. In a specific embodiment, the miRNA-762 inhibitor is a locked nucleic acid (LNA) oligonucleotide.

In some embodiments, the miRNA-762 inhibitor comprises a nucleotide sequence comprising at least 16 contiguous nucleotides complementary to the nucleotides of SEQ ID NO: 1. Additionally or alternatively, in some embodiments, the miRNA-762 inhibitor comprises the sequence of SEQ ID NO. 2 and modifications excluding base substitutions thereof, and fragments consisting of subsequences of SEQ ID NO: 2 of at least 8 contiguous nucleotides thereof.

In some embodiment, the miRNA-762 inhibitor includes one or more modifications. For example, in some embodiments, the miRNA-762 inhibitor is an oligonucleotide including a modification to enhance stability, potency, and/or specificity. Suitable modifications include, but are not limited to, a 2'-deoxy-2'-fluoro-beta-D-arabinose backbone.

In some embodiments, the miRNA-762 inhibitor is associated with a carrier molecule. For example, the carrier molecule could be selected from the group consisting of a nanoparticle, a liposome, and a lipoprotein.

In some embodiments, the miRNA-762 inhibitor includes one or more miRIDIAN inhibitors from Dharmacon, miScript from Quiagen, Anti-miR from Ambien, or MISSION from Sigma.

As noted herein above, the miRNA-762 inhibitor can be administered to a subject identified as having a risk of developing and/or a need for treatment of the condition associated with fibrosis and/or collagen deposition. In some embodiments, such condition can be selected from aortic stiffening/hypertension, vascular fibrosis, vascular disease, cardiovascular disease, interstitial pulmonary fibrosis, diastolic dysfunction, heart failure with preserved ejection fraction, renal fibrosis, pulmonary fibrosis, kidney fibrosis, lung fibrosis, atherosclerosis, fibrotic diseases/tissue fibrosis, systemic sclerosis, restenosis associated with vascular surgery (including but not limited to stenting or angioplasty), keloid formation, hypertrophic scars, fibromuscular dysplasia, systemic scleroderma, excessive scarring after surgery, myocardial fibrosis, esophageal stricture, joint contracture after immobilization, vascular inflammation, renal inflammation, cerebral inflammation, and Dupuytren's contracture.

In some embodiments, the subject is identified has having a risk of developing and/or a need for treatment of the condition associated with fibrosis and/or collagen deposition where there is an event creating such a risk. For example, a surgery can created a risk of fibrosis and/or collagen deposition. In this regard, in some embodiments, the miRNA inhibitor is administered following an event creating a risk of fibrosis and/or collagen deposition.

As used herein, the term "subject" refers to a target of administration and includes both human and animal subjects. Thus, veterinary therapeutic uses are provided in accordance with the presently disclosed subject matter.

In some embodiments, the subject does not have vascular calcification. Methods known to those skilled in the art can be used to assess whether a subject has vascular calcification, including, for example, computerized tomography (CT) scan.

In some embodiments, the subject has vascular fibrosis. Methods known to those skilled in the art can be used to assess whether a subject has vascular fibrosis, including, for example, pulse wave velocity (PWV).

Some embodiments of the methods disclosed herein involve administering an agent in addition to the miRNA-762 inhibitor. For example, in some embodiments, the method also involves administering an angiotensin-converting enzyme (ACE) inhibitors and/or angiotensin receptor blockers (ARB). Without wishing to be bound by theory or mechanism, miR-762 targets angiotensin converting enzyme, which makes angiotensin II. Thus to the extent that administration of the inhibitor increases production of angiotensin converting enzyme in certain subjects, ACE inhibitor or ARB could be co-administered. The method can also involve administering another antihypertensive agent, such as, for example, calcium channel blockers, diuretics, beta-adrenergic or alpha adrenergic blocking agents, sympatholytics, and thiazide diuretics. It is also contemplated that the miRNA-762 inhibitor could be given with and following renal sympathectomy as a co-treatment for hypertension and vascular stiffening.

In some embodiments, in addition to administration of the miRNA-762 inhibitor, a steroid can also be administered. Such co-administration is contemplated, for example, for treatment of keloids.

In some embodiments of the method, the inhibitor is administered at a site of fibrosis, scarring, or keloid. The inhibitor can be administered, for example, topically or by local injection. The inhibitor could also be administered intravenously either alone or associated with a carrier (e.g., targeted nanoparticle, liposome, etc.). In some embodiments, the inhibitor can be administered by intradermal injection. The inhibitor could also be administered by being associated with a device, such as a bandage or an implantable device coated with the inhibitor. In some embodiments, the device is a stent. In this regard, the presently-disclosed subject matter further includes a stent coated with an miRNA-762 inhibitor.

The presently-disclosed subject matter also includes a kit comprising a vial containing an miRNA-762 inhibitor and a device for use in a surgery creating a risk of fibrosis and/or collagen deposition. In some embodiments, the device is an angioplasty balloon. In some embodiments, the device is a stent.

The presently-disclosed subject matter also includes a pharmaceutical composition comprising: a miRNA-762 inhibitor and a second agent. In some embodiments, the second agent selected from the group consisting of: an angiotensin-converting enzyme (ACE) inhibitors, an angiotensin receptor blocker (ARB), another antihypertensive agent, and combinations thereof. In some embodiments, the another antihypertensive agent is selected from the group consisting of: calcium channel blockers, diuretics, beta-adrenergic or alpha adrenergic blocking agents, sympatholytics, and thiazide diuretics. In some embodiments, the second agent is a steroid. In some embodiments, the pharmaceutical composition further includes a pharmaceutically-acceptable carrier.

The presently-disclosed subject matter is further illustrated by the following specific but non-limiting examples. The following examples may include compilations of data that are representative of data gathered at various times during the course of development and experimentation related to the present invention.

EXAMPLES

The following studies were conducted to gain insight into microRNAs in the context of fibrosis and/or collagen deposition.

Example 1

Materials and Methods

Animals: Wild type mice were obtained from Jackson Laboratories on a C57Bl/6 background. At 3 months of age, these animals were implanted with telemetry units for measurement of blood pressure. One week later osmotic minipumps were implanted subcutaneously for infusion of angiotensin II (490 ng/kg/min) or vehicle for 2 weeks. Blood pressure was recorded for 10 minutes every hour for the duration of the experiments (i.e. three days prior to osmotic minipump implantation and until the end of angiotensin II infusion at Day 14). Hydralazine and hydrochlorothiazide were given in drinking water (320 mg/L and 60 mg/L) to normalize blood pressure at the same time as the 2 week angiotensin II infusion or to reverse established hypertension in the last two weeks of 4 week angiotensin II infusion. In deoxycorticosterone acetate (DOCA)-salt-treated mice, 100 mg deoxycorticosterone acetate pellet were implanted subcutaneously following uninephrectomy. These mice were subsequently maintained on drinking water with 0.9% NaCl for three weeks. AntagomiR-762, when applicable, was administered via retroorbita injection at a dose of 10 mg/mL at experimentally dictated intervals. At the end of each experiment, mice were sacrificed via CO2 inhalation and the chest was opened and the right atrium sectioned. A catheter was placed in the left ventricle and the animals were perfused with 0.9% saline at physiological pressure until the effluent is cleared of blood. The Institutional Care and Use Committee (IACUC) approved all experimental protocols.

Measurement of Aortic Collagen: Aortic collagen was visualized by Masson's Trichrome staining. Planimetry analysis was used to measure area of adventitial collagen.

Real-time PCR: RNA was extracted from freshly-harvested aorta or cell culture using Qiagen miRNeasy mini kit. cDNA was synthesized using ABI miRNA RT kit and pre-amplification reaction was performed using ABI Pre-Amp kit. The RT and TaqMan primer for mature mmu-miR-762 was obtained from Life technologies. qRT-PCR was performed using Applied Bioscience System 7500 Fast machine.

Matrix Array: RNA was extracted from freshly-harvested aorta or cell culture using Qiagen RNeasy mini kit. PCR array was performed to examine the expression of 84 genes for aortic matrix and adhesion molecules. Real time quantitative PCR was performed using Applied Bioscience System 7500 Fast machine.

Biaxial Mechanical Testing. Following overnight shipment in an iced physiologic solution, samples were cleaned of perivascular tissue and the intercostal branches were ligated using single strands from a braided 7-0 nylon suture. Vessels were then cannulated on pulled glass micropipets, secured with proximal and distal ligatures of 6-0 silk suture, and tested mechanically using a custom computer-controlled biaxial device. Briefly, following equilibration for approximately 30 minutes while submerged in a Hanks buffered physiologic solution (Invitrogen Life Technologies) at 37° C., the specimens were subjected to standard mechanical preconditioning consisting of 4 cycles of pressurization from 10 to 140 mmHg while the vessel was held near its in vivo axial length. Next, the unloaded configuration (outer diameter and axial length) was recorded, the in vivo axial stretch was estimated based on the force-pressure relationship, and the vessels were subjected to a series of 3 cyclic pressure-diameter protocols (from 10 to 140 mmHg at the in vivo and at ±5% of the in vivo axial stretch) and 4 cyclic axial force-length protocols (from 0 to 40 mN at constant pressures of 10, 60, 100, and 140 mmHg). Pressure, axial force, outer diameter, and axial length were recorded on-line over 2 cycles for all 7 protocols. To facilitate the computation of stress and strain, wall thickness was measured in the unloaded configuration which, via the assumption of incompressibility, allowed wall thickness to be calculated from the on-line measurements at all loaded (pressure and axial force) configurations.

Quantification of Mechanical Properties: It is well known in continuum biomechanics that a nonlinear (pseudo)elastic behavior is best described using a stored energy function W. Essentially, this function quantifies the energy stored within a tissue, per unit volume, upon mechanical loading and, consequently, the amount of energy available to the tissue to do work on its surroundings as it is unloaded. Moreover, first and second derivatives of W with respect to an appropriate measure of strain provide information, respectively, on the stress (a second order tensor) and the material stiffness (a fourth order tensor). Hence, this single scalar function provides a comprehensive quantification of the material behavior. Full details on the nonlinear mechanics of the arterial wall can be found elsewhere, as can details on the methods of quantifying both mean and layer-specific transmural wall properties and stresses in mice. For completeness, however, some of the primary equations are listed here.

Bulk Mechanical Properties—Studies of the effects of wall mechanics on hemodynamics (e.g., effects of arterial stiffness on pulse wave velocity) require information on the bulk (i.e., transmurally averaged) material properties. Toward this end, the biaxial mechanical data were first quantified using a validated nonlinear stress-strain relation that was derived from a homogenized, microstructurally-motivated elastic stored energy function W. Specifically, a "four-fiber family" form of W was used that was motivated by histological observations of nearly isotropically distributed elastin, four predominant families of locally parallel collagen fibers (axial, circumferential, and two symmetric diagonal), and circumferentially oriented smooth muscle. It is currently not possible to delineate contributions due to smooth muscle and circumferential collagen in the media, hence their contributions were treated phenomenologically via a single composite fiber family. Similarly, it is currently not possible to delineate effects of cross-links or physical entanglements, hence the parameters characterizing W (see below) were determined via nonlinear regression using the collected macroscopic data (see Table S2), thus yielding a sufficient phenomenological descriptor for studying fluid-solid-interactions. This stored energy function can be written $$W(C, M^j) = \frac{c}{2}(I_C - 3) + \sum_{j=1}^{4} \frac{c_1^j}{4c_2^j} \{\exp[c_2^j(IV_C^j - 1)^2] - 1\}, \quad (S.1)$$

where $c$, $c_1^j$, and $c_2^j$ ($j=1,2,3,4$) are model parameters, with $c$ and $c_1^j$ having units of stress (kPa) and $c_2^j$ dimensionless, $C=F^TF$ is the right Cauchy-Green deformation tensor, and F is the deformation gradient tensor. $M^j=[0, \sin\alpha_0^j, \cos\alpha_0^j]$ is a unit vector in the direction of the $j^{th}$ fiber family, where the angle $\alpha_0^j$ is computed relative to the axial direction in a reference configuration. Thus, axial and circumferential fiber families are oriented at $\alpha_0=0$ and $\alpha_0=90$ degrees, respectively. In addition, $I_c=\text{tr}(C)$ and $IV_c^j=M^j \cdot CM^j$ are coordinate invariant measures of deformation that can be written in terms of stretch ratios, namely $$I_C = \lambda_\vartheta^2 + \lambda_z^2 + \frac{1}{\lambda_\vartheta^2 \lambda_z^2}, \; IV_C^j = \lambda_\vartheta^2 \sin^2 \alpha_0^j + \lambda_z^2 \cos^2 \alpha_0^j, \quad (S.2)$$

for $F=\text{diag}(\lambda_r, \lambda_\theta, \lambda_z)$, noting that incompressibility requires $\lambda_r = 1/(\lambda_\theta \lambda_z)$. The Cauchy stress tensor $\sigma$ can then be computed as $$\sigma = -pI + 2F \frac{\partial W}{\partial C} F^T, \quad (S.3)$$

where I is the second order identity tensor, the superscript T indicates the transpose of the tensor, and p is a Lagrange multiplier that enforces the incompressibility.

Clearly, then, the biaxial stresses could be calculated easily from W for all 7 biaxial testing protocols given the on-line measurements of the deformations and values of the 8 model parameters. Best-fit values of these parameters were determined from the biaxial data using a nonlinear regression algorithm that minimized an objective function based on the sum-of-the-squares of differences between measured and predicted normalized pressures and axial forces. Toward this end, note that a 2-D formulation was adopted (i.e., the radial stress relative to the circumferential and axial stresses was neglected), hence expressions for pressure and force were obtained directly by inverting global equilibrium equations for stress, namely solving $$\sigma_\vartheta = \langle \sigma_{\vartheta\vartheta} \rangle = \frac{Pa}{h}, \; \sigma_z = \langle \sigma_{zz} \rangle = \frac{f}{\pi h(2a+h)} \quad (S.4)$$

for the transmural pressure P and the total axial force on the vessel $f=f_T + \pi a^2 P$ (with $f_T$ representing the transducer-measured axial force), where a is the measured inner radius and h is the wall thickness, both in the loaded configurations. In this way, the best-fit model parameters assured that the resulting stress-strain relation satisfied equilibrium at each pressurized and axially loaded state. Given these parameter values, mean wall stress, material stiffness, and overall elastic energy storage could be computed for any deformation, in vitro or in vivo, all of which were computed and compared between the Sham and Ang II treated vessels at both mean and systolic pressures (see Table S1). Note, therefore, that the components of the linearized stiffness tensor ($\mathscr{C}_{ijkl}$) were computed as, $$\mathscr{C}_{ijkl} = 2\delta_{ik} F_{iA}^o F_{jB}^o \frac{\partial W}{\partial C_{AB}} + \quad (S.5)$$

$$2\delta_{jk} F_{iA}^o F_{iB}^o \frac{\partial W}{\partial C_{AB}} + 4F_{iA}^o F_{jB}^o F_{kP}^o F_{lQ}^o \frac{\partial^2 W}{\partial C_{AB} \partial C_{PQ}}\bigg|_{C^o},$$

where $\delta_{ij}$ are the components of the second order identity tensor I, $F^o$ is the deformation gradient tensor that maps the chosen reference configuration into a finitely deformed in vivo configuration, and $C^o$ is the corresponding right Cauchy-Green deformation tensor. By linearizing about an appropriate in vivo state, one obtains directly the values of material stiffness that are needed in computational models of effects of the wall mechanics on the hemodynamics. Finally, the often used structural parameter called distensibility was computed and compared $$D=[d_{sys}-d_{dias}]/[(d_{dias})(P_{sys}-P_{dias})], \quad (S.6)$$

where d is the outer diameter, and sys and dias denote, respectively, the systolic and diastolic values of diameter and pressure.

Transmural Stress Distributions—Studies of arterial mechanobiology require separate information on the properties of and stresses within the media and adventitia. Hence, the biaxial data were further analyzed using a novel bi-layered model of the arterial wall. Briefly, this model is based on layer-specific stored energy functions that are similar to that used to model the mean behavior of the wall, though with some subtle differences. Whereas classical analyses of wall stress use an unloaded reference configuration, the structurally-motivated, layer-specific relations accounted for the different constituents (e.g., elastic fibers or multiple families of collagen fibers) having different "pre-stresses" in a homeostatic in vivo configuration, which was used as a computational reference. These pre-stresses result from constituent-specific deposition stretches, which were estimated by recording changes in dimensions before and after elastase exposure (see Biaxial Mechanical Testing). While the 8 constituent-specific model parameters were prescribed to be the same in the two layers of the arterial wall, differences in their relative abundance ($\phi^i$, area fractions as estimated from the histological image analysis) endowed the media and adventitia with different mechanical responses.

In particular, it was assumed a mass-averaged stored energy function of the form:

$$W = \phi^e W^e(F^e) + \phi^m W^m(\lambda^m) + \sum_{j=1}^{4} \phi^{cj} W^{cj}(\lambda^{cj}) \quad (S.7)$$

where the superscripts i=e, m and c refer to elastic fibers, smooth muscle, and each of four families of collagen fibers (j=1,2,3,4), $\phi^i$ and $W^i$ are the mass fractions and the stored energy functions for the constituents that compose the mixture, $F^e$ is the deformation gradient tensor experienced by the elastic fibers, and $\lambda^m$ and $\lambda^{cj}$ are the stretches experienced by the smooth muscle and the $j^{th}$ family of collagen fibers.

Similar to Equation S.1, the behavior of the elastic fibers was described by a neo-Hookean stored energy function $$W^e = \frac{c^e}{2}(I_{C^e} - 3), \quad (S.8)$$

where $c^e$ is a material parameter with the dimension of a stress (kPa), $i_{C^e}=\text{tr}(C^e)$, $C^e=F^{e^T}F^e$ and $F^e=FG_h^e$, with $G_h^e$ the deposition stretch tensor between the natural (stress-free) configuration of the elastic fibers and the homeostatic reference configuration, with F depending on the specific deformation of the wall. Furthermore, $G_h^e$ was assumed to be principal, with the circumferential deposition stretches within the interval [1.94, 2.05] for the Sham and [1.39, 1.84] for the Ang II treated vessels, the axial deposition stretches within the interval [1.55, 1.60] for the Sham and [1.26, 1.52] for the Ang II treated vessels, and the radial deposition stretch computed based on incompressibility.

The nonlinear response of collagen fibers, resulting from the progressive engagement of undulated fibers, was modeled using a Fung-type exponential relationship. Again, because it is not possible to delineate the behavior of circumferentially oriented collagen fibers in the media and associated smooth muscle, their combined contributions were similarly modeled using a Fung exponential. Hence, $$W^m = \frac{c_1^m}{4c_2^m}[e^{c_2^m(IV^m-1)^2} - 1], \tag{S.9}$$

$$W^{cj} = \frac{c_1^c}{4c_2^c}[e^{c_2^c(IV^{cj}-1)^2} - 1], \tag{S.10}$$

where $c_1^m$ and $c_1^c$ are model parameters with the dimension of a stress (kPa), while $c_2^m$ and $c_2^c$ are dimensionless. Neither the smooth muscle nor the collagen fibers were assumed to have any radial orientation. The stretch experienced by smooth muscle was thus obtained by projecting C along the cell axis, $$\lambda^m = \sqrt{IV^m} = G_h^m \sqrt{C:(M^m \otimes M^m)}, \tag{S.11}$$

where $G_h^m$ is the deposition stretch between the natural (stress-free) and homeostatic (reference) configurations, and $M^m = [0, \sin \alpha_0^m, \cos \alpha_0^m]$ is a unit vector representing smooth muscle cell orientation in the reference configuration. $G_h^m$ was assigned within the range [1.10, 1.12] for both experimental groups. Similarly, for the stretch in the direction of the collagen fibers, $$\lambda^{cj} = \sqrt{IV^{cj}} = G_h^{cj}\sqrt{C:(M^{cj} \otimes M^{cj})}, \tag{S.12}$$

where $G_h^{cj}$ is the deposition stretch and $M^{cj} = [0, \sin \alpha_0^{cj}, \cos \alpha_0^{cj}]$ is a unit vector that identifies the dominant orientation of the $j^{th}$ family of collagen fibers. Values of $G_h^{cj}$ within the interval [1.04, 1.06] were assigned to each family of collagen fibers for both the Sham and the Ang II treated vessels. Two additional parameters, $\beta_\theta$ and $\beta_z$, which describe the portion of collagen fibers oriented circumferentially and axially, respectively, were also estimated from experimental data, bringing the total count of estimated tensile parameters to 8 (see Table S3).

Because the components of stress and stiffness are defined pointwise, the components of Cauchy stress ($\sigma_{ij}$) and linearized stiffness ($\mathscr{E}_{ijkl}$) were again computed using Equations S.3 and S.5, where the contribution of each constituent was modulated by the associated mass fractions $\phi^i$ and specific deformations experienced by the elastic fibers, smooth muscle, and collagen fibers were accounted for through their unique deposition stretches $G_h^i$. Once the material properties were known, classical relations were used to enforce equilibrium under the different pressure—axial load conditions, which in turn allowed the calculation of transmural distributions of wall stress.

Statistical Analysis: Data are expressed as mean±SEM. Comparisons were made with either a Student's T-test, 1-way or 2-way ANOVA when indicated.

Results and Discussion

To gain insight into how microRNAs might affect hypertension, RNA was isolated from sham and angiotensin II-infused mouse aortas and a miRNA array was performed. While several were upregulated in the hypertensive aorta, the present inventors chose to focus on miR-762 because it was the most abundant and is present in both humans and mice. It was confirmed that miR-762 was upregulated by chronic angiotensin II infusion using qRT-PCR of whole aortic RNA (FIG. 1A-B).

Figure 1B:
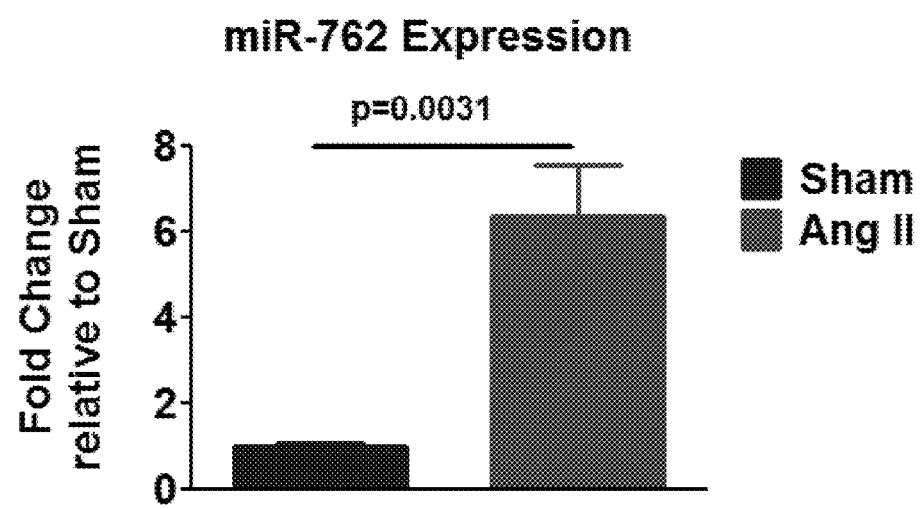

Reference is made to FIG. 1A-B, which illustrate the effect of angiotensin II-induced hypertension on vascular miR-762. C57Bl/6 mice received angiotensin II (490 ng/kg/min) or sham for two weeks. Immediately after euthanasia, thoracic aortas were harvested for RNA extraction. cDNA was reverse transcribed and qRT-PCR for miR-762 performed. The results indicate that Ang II leads to a significant upregulation in vascular miR-762.

To determine if miR-762 expression is due to a direct effect of angiotensin II or if it is due to mechanical stretch, 2 additional mouse models were utilized. To prevent hypertension-related mechanical stretch, Hydralazine (320 mg/mL) and Hydrochlorothiazide (60 mg/mL) was administered in the drinking water during angiotensin II infusion to half of the animals. As another approach, mice with deoxycorticosterone acetate (DOCA) salt hypertension were created as previously described and utilized by the present inventors. This model is dependent on sodium and volume and is associated with suppression of the renin-angiotensin system. This experiment revealed that miR-762 upregulation in hypertension is a direct effect of Ang II as lowering BP with hydralazine and hydrochlorothiazide (hyd/HCTZ) did not prevent Ang II induced miR-762 upregulation. In addition, DOCA salt hypertension only led to a minor, albeit, significant increase in miR-762 levels (FIG. 2).

Figure 2:
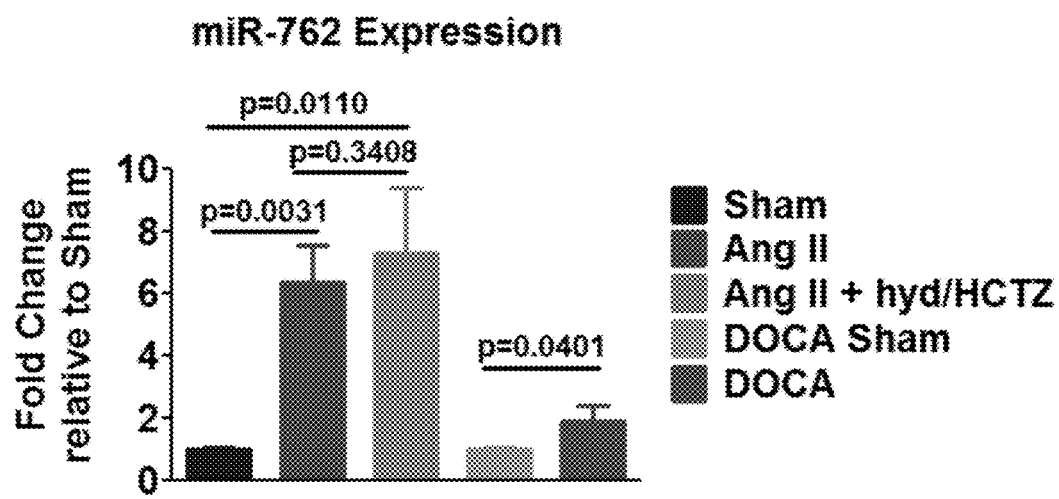
FIG. 2 shows a graph illustrating that miR-762 upregulation in hypertension is a direct effect of angiotensin II. C57Bl/6 mice received angiotensin II (490 ng/kg/min) with and without co-treatment with hydralazine and hydrochlorothiazide (hyd/HCTZ, dose) or sham for two weeks. In another group, DOCA-salt hypertension was induced in C57Bl/6 mice whereby mice undergo a unilateral nephrectomy and a DOCA pellet implanted subcutaneously. Subsequently, these mice were given 1% salt in drinking water for three weeks. Immediately after euthanasia, thoracic aortas were harvested for RNA extraction. cDNA was reverse transcribed and qRT-PCR for miR-762 performed.

With reference to FIG. 2, miR-762 upregulation in hypertension is a direct effect of angiotensin II. C57Bl/6 mice received angiotensin II (490 ng/kg/min) with and without co-treatment with hydralazine and hydrochlorothiazide (hyd/HCTZ, dose) or sham for two weeks. In another group, DOCA-salt hypertension was induced in C57Bl/6 mice whereby mice undergo a unilateral nephrectomy and a DOCA pellet implanted subcutaneously. Subsequently, these mice were given 1% salt in drinking water for three weeks. Immediately after euthanasia, thoracic aortas were harvested for RNA extraction. cDNA was reverse transcribed and qRT-PCR for miR-762 performed.

To determine the effect of miR-762 loss of function on blood pressure during Ang II infusion, blood pressure was measured via telemetry. Briefly, telemeters were implanted, as previously done by the present inventors. Ten days later, osmotic mini pumps were implanted for delivery of angiotensin II (490 ng/kg/min) or vehicle for two weeks. The miR-762 inhibitor (antagomiR-762) or vehicle (PBS) was administered at days 0, 3 and 7. AntagomiR-762 did not influence BP in response to either Ang II or Sham (FIG. 3).

Figure 3:
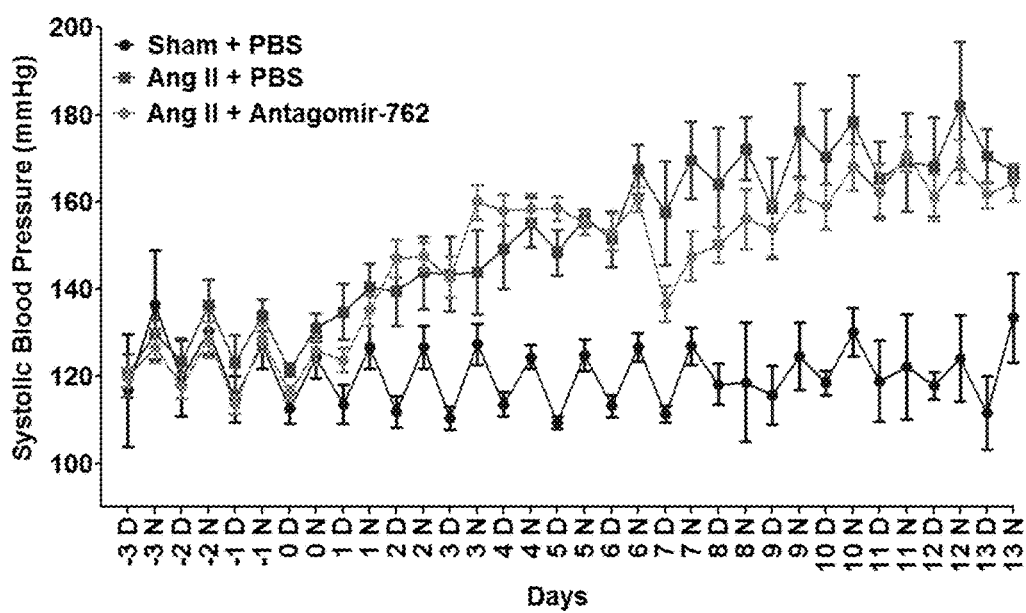
FIG. 3 shows a graph illustrating that antagomiR-762 treatment did not alter Ang II induced hypertension. Telemetric measurement of blood pressure in conscious mice infused with angiotensin II or sham treated with antagomiR-762 (day 0, 3 and 7) or vehicle (PBS).

With reference to FIG. 3, showing the results of telemetric measurement of blood pressure in conscious mice infused with angiotensin II or sham treated with antagomiR-762 (day 0, 3 and 7) or vehicle (PBS). AntagomiR-762 treatment did not alter Ang II induced hypertension.

Figure 4A:
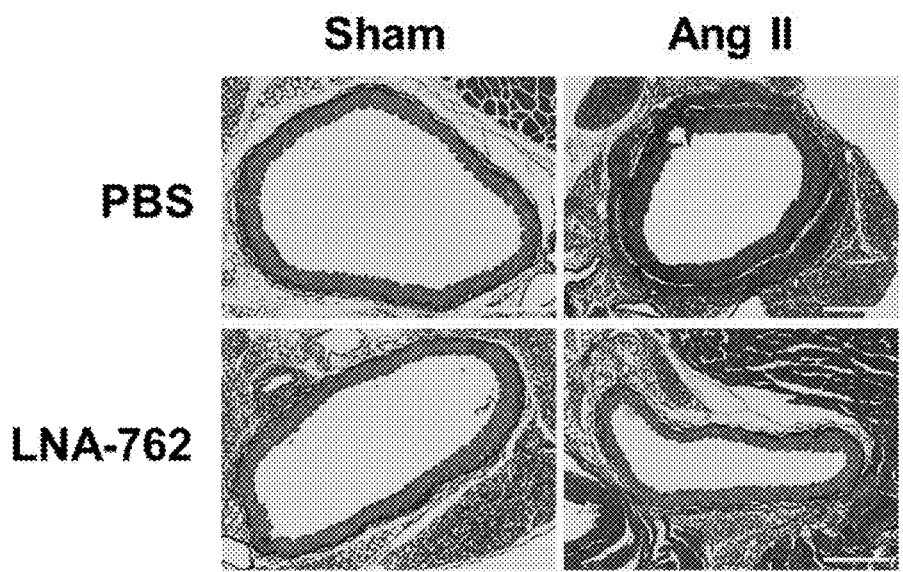
FIG. 4A-C shows images and graphs illustrating that miR-762 inhibition prevents Ang II-induced aortic fibrosis. C57Bl/6 mice received sham or angiotensin II (490 ng/kg/min) for 2 weeks with and without co-treatment with LNA-762. (A) Images of Masson's trichrome stained aortas from mice infused with Ang II and co-treated with either PBS or LNA-762 showing the prevention of aortic fibrosis in the aortas of Ang II infused mice co-treated with LNA-762. (B) Graph showing aortic adventitial collagen quantified using planimentry analysis from images of Masson's trichrome stained aortas. (C) Graph showing hydroxyproline measurement of collagen content from the aortas of the same treatment groups as above.
Figure 4B:
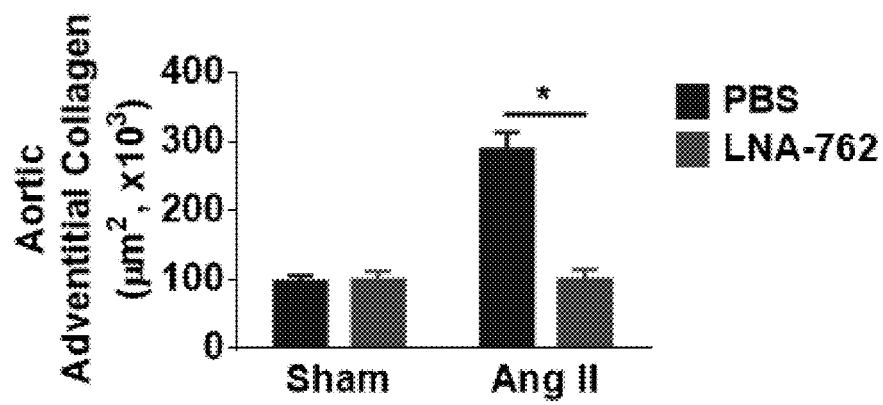
Figure 4C:
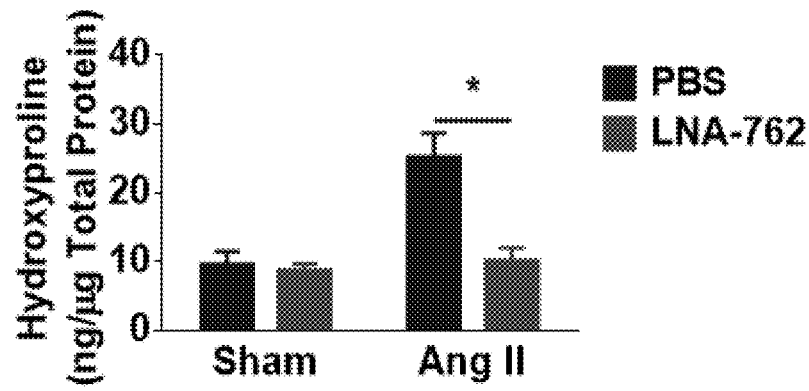

However, despite significant elevation in BP, with reference to FIG. 4A-C, mice that received Ang II and an miR-762 inhibitor (e.g., LNA-762) did not show aortic adventitial fibrosis (FIG. 4A-C). This suggests that LNA-762 protects mice from Ang II induced vascular remodeling and fibrosis.

Figure 5:
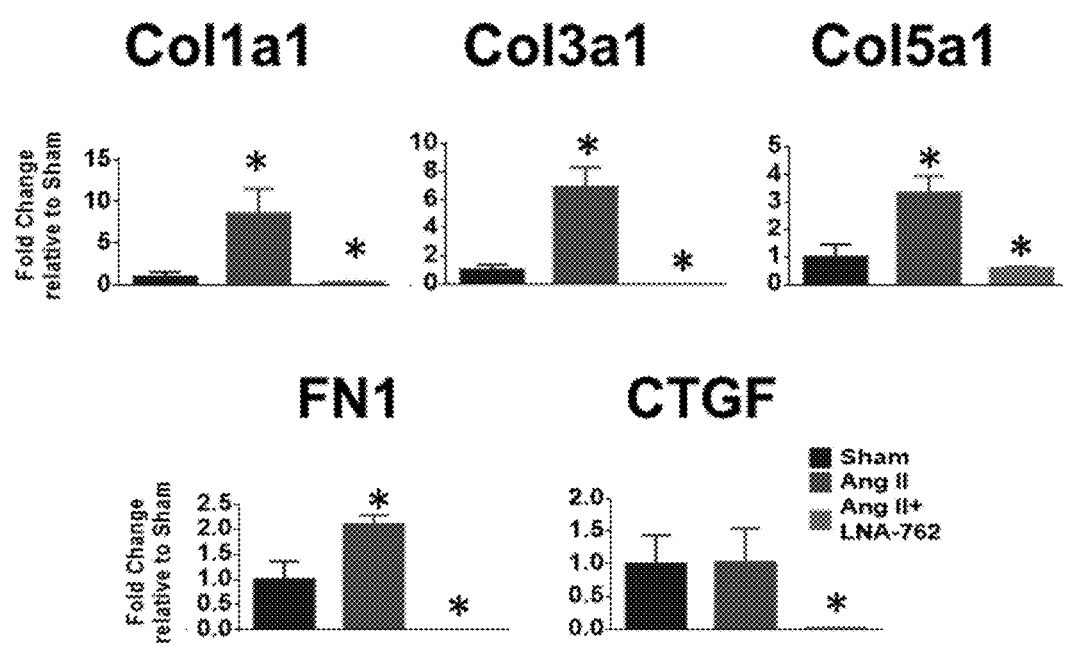
FIG. 5 shows graphs illustrating that miR-762 inhibition prevents Ang II induced upregulation in the expression of pro-fibrotic proteins. C57Bl/6 mice received sham or angiotensin II (490 ng/kg/min) for 2 weeks with and without co-treatment with LNA-762. Using a matrix qPCR array, the expression of 86 matrix important genes were analyzed. Representative pro-fibrotic genes are shown here.
Figure 6:
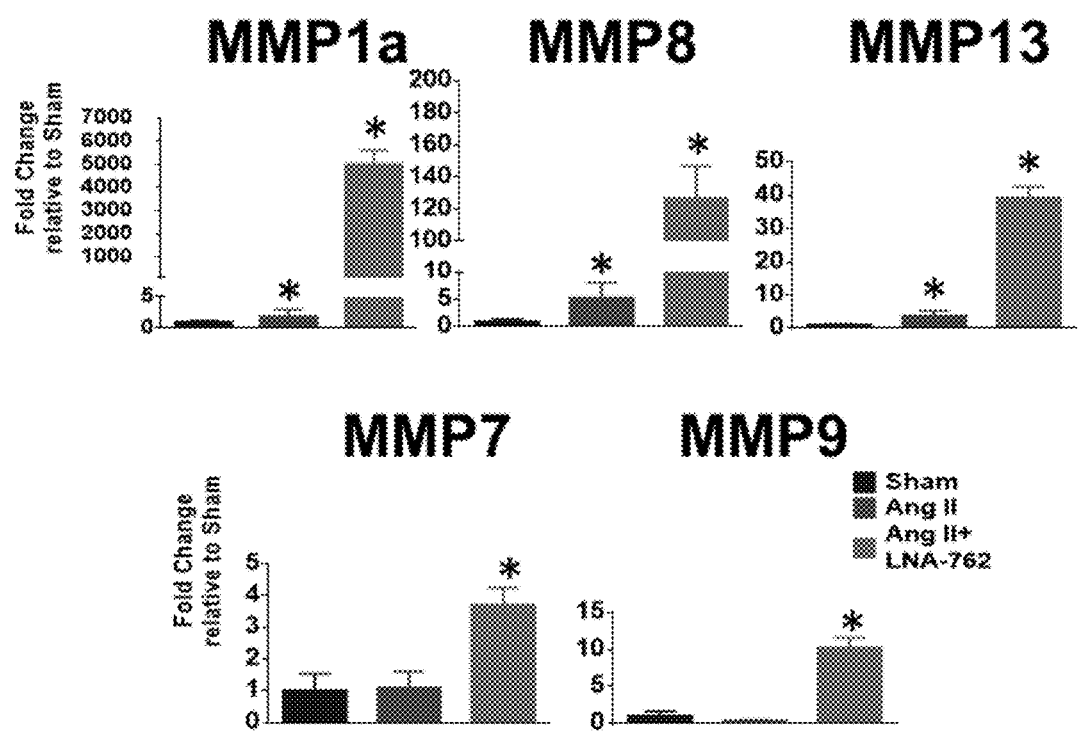
FIG. 6 shows graphs illustrating that miR-762 inhibition promotes the upregulation of matrix degrading matrix metalloproteinases (MMPs). C57Bl/6 mice received sham or angiotensin II (490 ng/kg/min) for 2 weeks with and without co-treatment with LNA-762. Using a matrix qPCR array, the expression of 86 matrix important genes were analyzed. Representative matrix degrading MMP genes are shown here.

To uncover the possible molecular mechanisms underlying the effects of miR-762 inhibition on vascular matrix deposition, the expression profile of 86 matrix associated genes was analyzed using an Illumina Matrix Gene Array from the aortas of mice treated with Ang II or Sham, co-treated with either LNA-762 or vehicle (PBS). This assay showed that LNA-762 treatment causes a dramatic downregulation of pro-fibrotic genes such as Collagens, connective tissue growth factor (CTGF), and fibronectin, and a dramatic upregulation in matrix degrading genes matrix metalloproteinases (MMPs) (FIGS. 5 and 6). This suggests that miR-762 promotes fibrosis by promoting the expression of pro-fibrotic genes and decreases the expression of matrix degrading genes. The precise molecular mechanisms underlying these phenomena remains to be elucidated.

The aorta's Windkessel function is important in the maintenance of a constant blood pressure during the cardiac cycle. Aortic stiffness, which accompanies and leads to hypertension, is characterized by loss of aortic compliance and increases predisposition to strokes, renal failure and myocardial infarction.

Figure 7A:
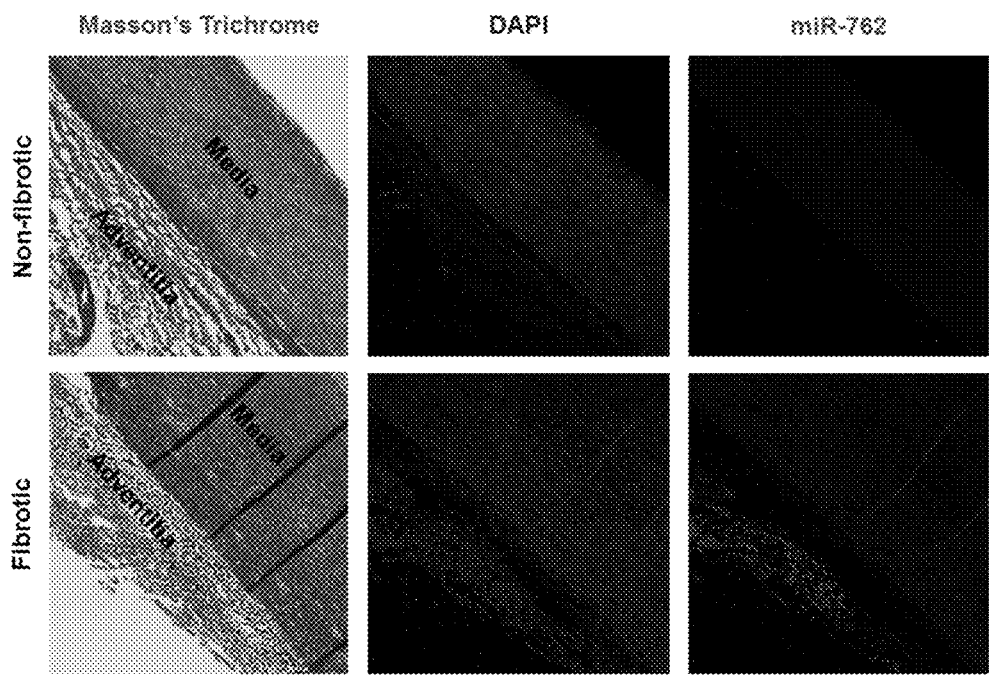
FIG. 7A-B show images illustrating localization and upregulation of miR-762. (A) Images showing that miR-762 expression is upregulated in humans exhibiting aortic fibrosis and is primarily localized in the adventitia. More specifically, the images show Masson's trichrome staining and in situ hybridization of human aortic sections showing a correlation of fibrosis with miR-762 staining. (B) Images showing that miR-762 expression is upregulated after Ang II infusion and primarily localized in bone marrow derived cells in the adventitia. In situ hybridization for miR-762 from the aortas of lethally irradiated mice transplanted with EGFP+ bone marrow and infused with Ang II.
Figure 7B:
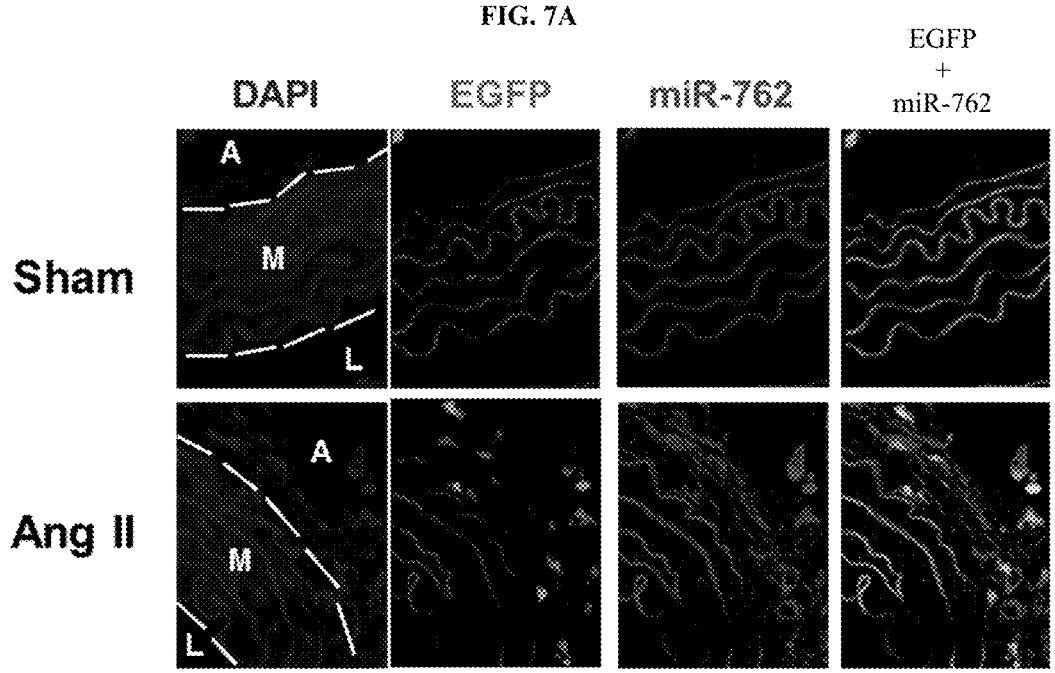
Figure 8A:
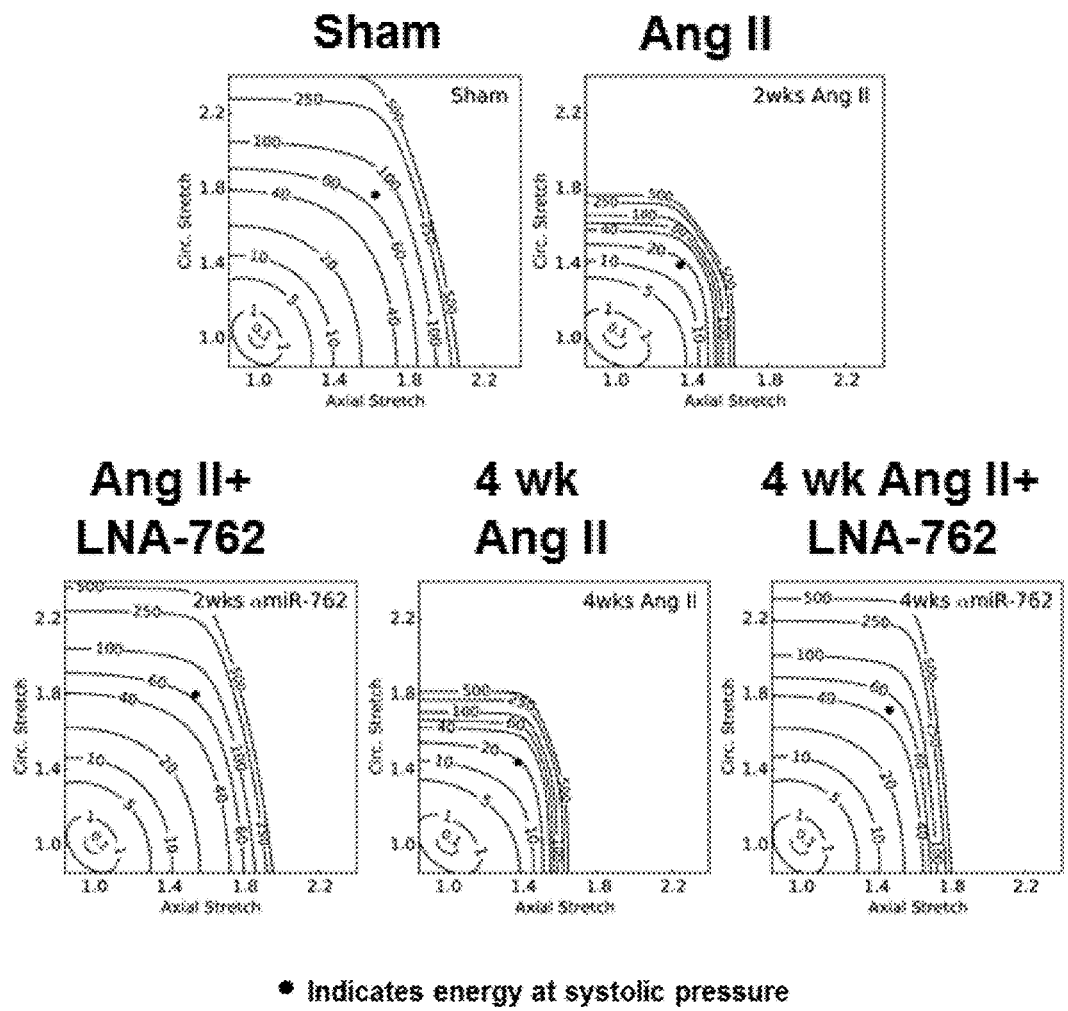
FIG. 8A-B show graphs illustrating that miR-762 inhibition prevents and reverses Ang II inducted aortic stiffening. Using a pressure myograph device multiple biomechanical properties of the aorta were calculated, including stretch, stress and strain, which in combination with the mice's blood pressure, were used to calculate the aorta's systolic energy storage capacity. (A) Representative stretch contour plots for each condition tested (B) Systolic energy storage values of the aorta.
Figure 8B:
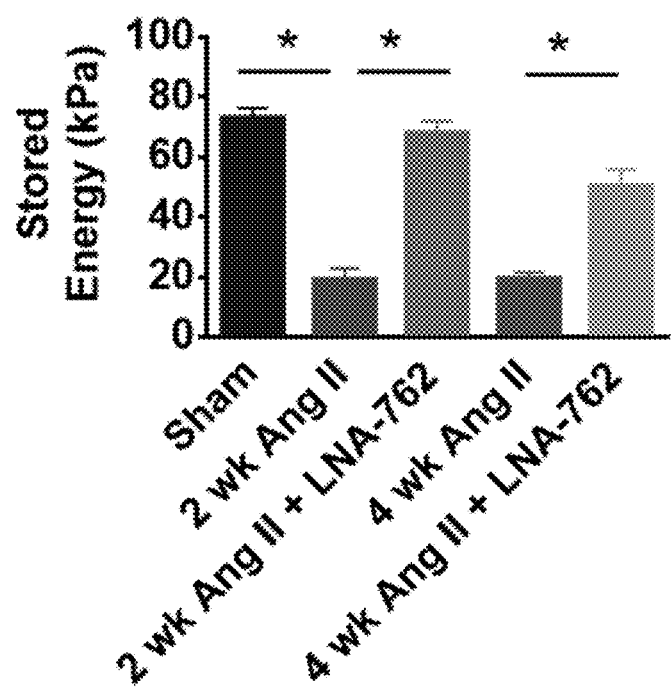

The present inventors have shown that aortic stiffness is accompanied and is due to the accumulation of collagens in the aortic adventitia. Additionally, as illustrated in FIG. 7A, the instant inventors have shown that miR-762 expression is upregulated in humans exhibiting aortic fibrosis and is primarily localized in the adventitia. More specifically, FIG. 7B shows that upregulated miR-762 expression after Ang II infusion is primarily localized in bone marrow derived cells in the adventitia. Furthermore, as described herein, the present inventors have shown that miR-762 inhibition prevents Ang II induced fibrosis, and thus sought to determine the effects of miR-762 inhibition in aortic compliance. To do this, the biomechanical properties of the dorsal thoracic aortas of mice treated with Ang II, Sham, or Ang II+LNA-762 were measured. Energy stored during systole was calculated using the formula S.1 (FIG. 8A-B). A summary of the effects of antagomiR-762 on aortic fibrosis, stiffening, and matrix gene expression are also shown below in Table 2.

compared to Ang II infused controls, suggesting that LNA-762 led to increased aortic compliance, which is likely indicative of a reversal in fibrosis. Further studies are necessary to elucidate the precise mechanisms on how this phenomenon occurs.

In conclusion, miR-762 was found to be highly upregulated in hypertension as a direct effect of Ang II. In addition, it was shown that miR-762 promotes fibrosis and that in vivo inhibition of miR-762 prevents and reverses Ang II induced aortic fibrosis and stiffness. It is contemplated that miR-762 inhibitors could be useful as a therapy in the treatment of aortic stiffening and/or other conditions associated with fibrosis and/or collagen deposition, which is an unmet medical need.

Example 2

Figure 9:
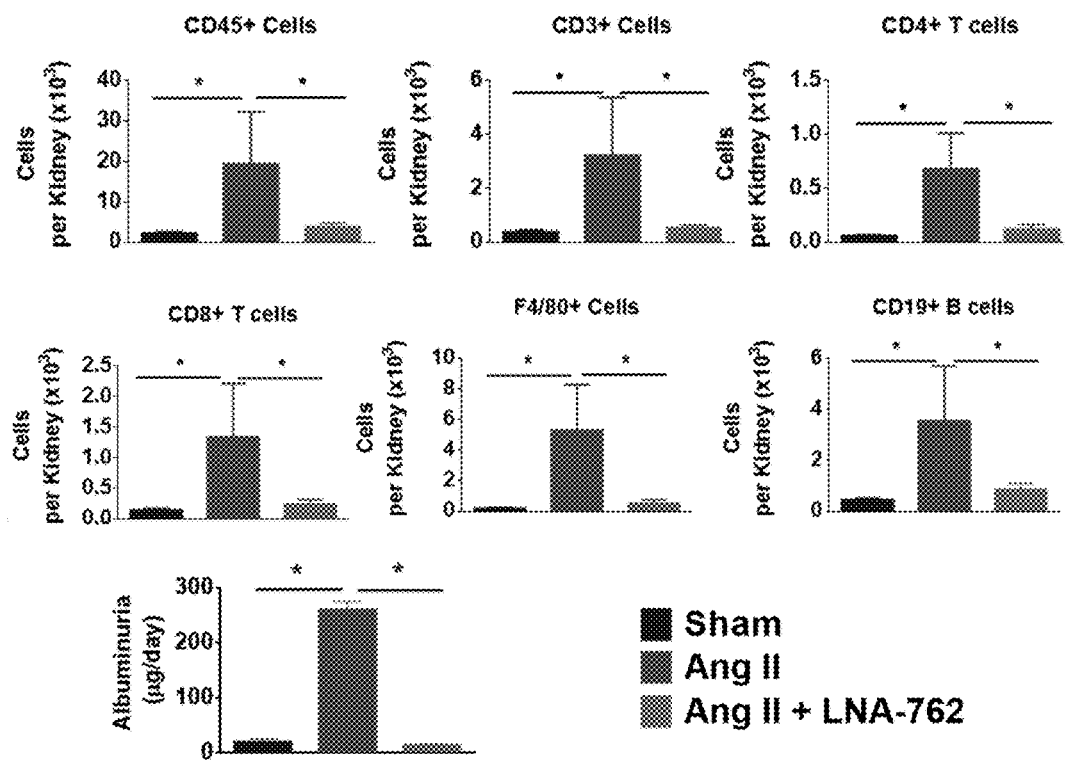
FIG. 9 shows that miR-762 inhibition prevents Ang II induced renal damage. Using flow cytometry, the infiltration of CD45+, CD3+, CD4+, Cd8+ F4/80+, and CD19+cells were quantified in kidney single cell suspension from mice infused with sham or Ang II and treated with either PBS or LNA-762. 24-hour urinary albumin excretion was quantified by ELISA from urine collected over a 24-hour period.

To determine the effects of miR-762 inhibition on kidney damage mice were infused with sham or Ang II and treated with either PBS or LNA-762, then the infiltration of various cells was quantified in kidney single cell suspension using flow cytometry. As illustrated in FIG. 9, Ang II promotes the infiltration of inflammatory cells CD45+, CD3+, CD4+, Cd8+, F4/80+, and CD 19+ into the kidney, which was prevented by the inhibition of miR-762 with LNA-762. 24-hour urinary albumin excretion was also quantified by ELISA from urine collected over a 24-hour period. These results indicate that miR-762 inhibition prevents HTN-induced Kidney damage as well as Ang II induced albuminuria.

Figure 10:
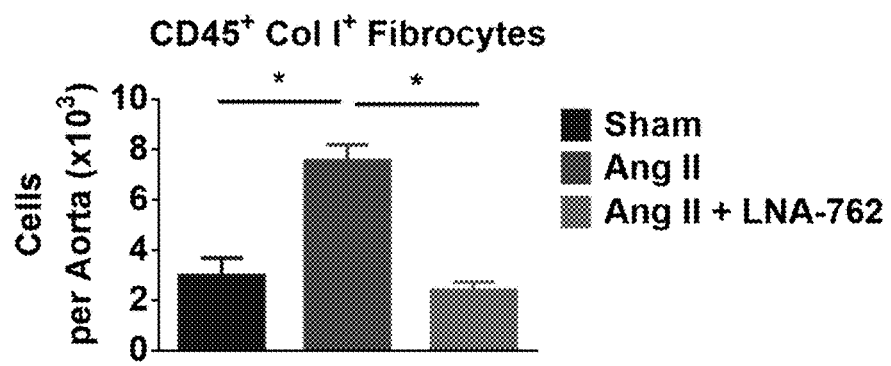
FIG. 10 shows a graph illustrating that miR-762 inhibition decreases HTN induced fibrocyte infiltration in the aorta. Using flow cytometry, the number of infiltrating CD45+ and Col I+ cells in the aorta was quantified from mice infused with Ang II and treated with either PBS or LNA-762.

Referring to FIG. 10, it was also shown that miR-762 inhibition decreases HTN induced fibrocyte infiltration in the aorta. Using flow cytometry, the number of infiltrating

TABLE 2

|  | Sham | Ang II | Ang II + AntagomiR-762 | P value (One way ANOVA) |
|---|---|---|---|---|
| Adventitial Collagen ($\mu m^2$) | 7,579 ± 10,055 | 283,927 ± 15,595 | 79,872 ± 7,113 | <0.0001 |
| Systolic energy storage ($W_{sys}$, kPa) | 66 ± 2.49 | 17 ± 1.33 | 61 ± 4.73 | <0.0001 |
| Collagen 1α1* | 1.0 ± 0.55 | 8.56 ± 2.95 | 0.36 ± 0.04 | 0.0149 |
| Collagen 3α1* | 1.0 ± 0.35 | 6.93 ± 1.37 | 0.00025 ± 0.000018 | 0.0004 |
| Collagen 5α1* | 1.0 ± 0.44 | 3.34 ± 0.61 | 0.59 ± 0.06 | 0.0033 |
| Fibronectin 1* | 1.0 ± 0.36 | 2.10 ± 0.18 | 0.00048 ± 0.000055 | 0.0004 |
| MMP1a* | 1.0 ± 0.21 | 1.84 ± 1.12 | 5,010 ± 600 | <0.0001 |
| MMP8* | 1.0 ± 0.34 | 5.27 ± 2.83 | 126.74 ± 20.09 | <0.0001 |
| MMP13* | 1.0 ± 0.21 | 3.76 ± 1.55 | 39.35 ± 3.22 | <0.0001 |

All values are presented as mean ± SE.
*Note:
All fold change values were normalized to the sham group.

These data show that Ang II causes a dramatic decrease in stored energy compared to sham indicative of aortic stiffening. However, co-treatment of Ang II with LNA-762 prevents Ang II-induced aortic stiffness. The current understanding of fibrosis and aortic stiffness is that after it is established, it is irreversible. However, the results with the matrix array shown above suggest that LNA-762 promotes the upregulation of matrix degrading MMPs. Hence, it is possible that LNA-762 could reverse fibrosis via the degradation of established collagenous deposits. To determine if LNA-762 can reverse established aortic fibrosis and stiffness, LNA-762 (day 14, 17, 21) was administered after 14 days of Ang II infusion, while still receiving Ang II. Aortas from mice that received LNA-762 after establishment of aortic stiffness treatment show increased energy storage CD45+ and Col I+ cells was quantified in the aorta from mice infused with Ang II and treated with either PBS or LNA-762.

Example 3

Figure 11:
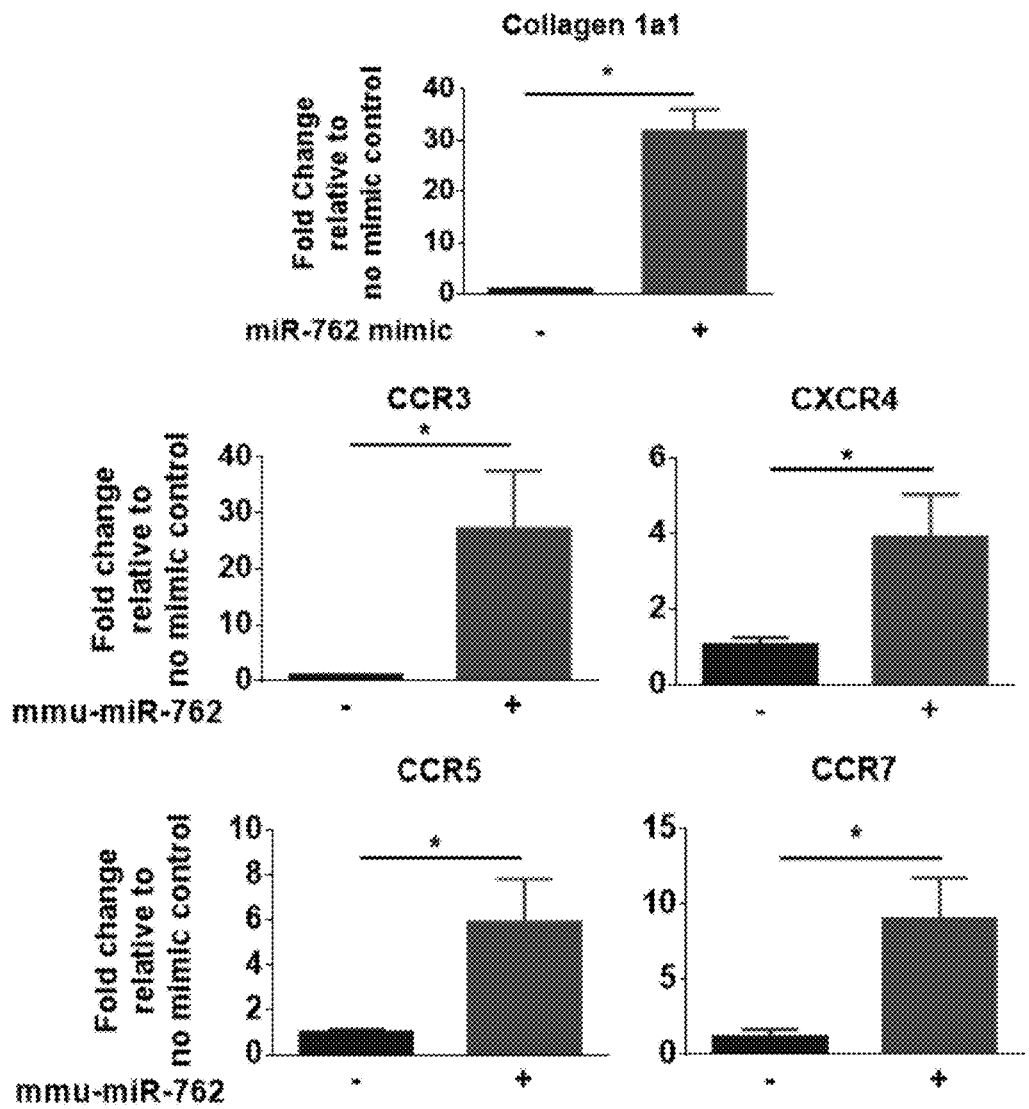
FIG. 11 shows graphs illustrating that miR-762 induces collagen and chemokine receptor mRNA production in bone marrow cells. Bone marrow cells were transfected with miR-762 mimic, and total RNA was harvested after 72 hours. Using qRT-PCR, the expression of Collagen I, CCR3, CXCR4, CCR5 and CCR7 was measured.

To determine the effects of miR-762 on bone marrow cells, the cells were transfected with miR-762 mimic and total RNA was harvested after 72 hours. Using qRT-PCR, the expression of Collagen I, CCR3, CXCR4, CCR5 and CCR7 was then measured. As illustrated in FIG. 11, this indicated that miR-762 induces collagen and chemokine receptor mRNA production in bone marrow cells. More specifically, miR-762 promotes the transformation of bone marrow cells to a collagen producing/fibrocyte-like phenotype and promotes their homing to injury sites.

Throughout this document, various references are mentioned. All such references are incorporated herein by reference, including the references set forth in the following list:

REFERENCES

1. Gui, et al., "MicroRNAs that target Ca$^{2+}$ transporters are involved in vascular smooth muscle cell calcification," *Laboratory Investigation* (2012) 92, 1250-1259.
2. Tsao, et al., "Cross-Sectional Relations of Arterial Stiffness, Pressure Pulsatility, Wave Reflection, and Arterial Calcification," *Arterioscler Thromb Vasc Biol* (2014) 2495-2500.
3. U.S. Patent Application Publication No. 2013/0216605.
4. U.S. Patent Application Publication No. 2013/0005658.
5. U.S. Patent Application Publication No. 2012/0165392.

All publications, patents, and patent applications mentioned in this specification are herein incorporated by reference to the same extent as if each individual publication, patent, or patent application was specifically and individually indicated to be incorporated by reference.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A treatment method for HTN-induced kidney damage, Ang II induced aortic fibrosis, or upregulation of matrix degrading matrix metalloproteinases (MMPs), comprising:
   administering an effective amount of a miRNA-762 inhibitor to a subject;
   wherein the subject is in need of treatment for HTN-induced kidney damage, Ang II induced aortic fibrosis, or upregulation of matrix degrading MMPs.

2. The method of claim 1, and further comprising determining the levels of miR-762 in a sample from the subject.

3. The method of claim 2, wherein the sample includes excess levels of miR-762 as compared to a control.

4. The method of claim 1, wherein the miRNA-762 inhibitor is an oligonucleotide of 8-49 nucleotides in length having a sequence targeted to miRNA-762, or a precursor thereof.

5. The method of claim 4, wherein the oligonucleotide is an antisense oligonucleotide that is at least partially complementary to the sequence of the target miRNA, or a precursor thereof.

6. The method of claim 5, wherein the antisense oligonucleotide is selected from the group consisting of a ribonucleotide, a deoxyribonucleotide, an anti-sense molecule, a siRNA molecule, a shRNA molecule, a miRNA sponge, a cDNA, an antagomir, a locked nucleic acid (LNA) oligonucleotide, a decoy oligonucleotide, a peptide nucleic acid (PNA), a morpholino oligonucleotide, or a combination thereof.

7. The method of claim 5, wherein the oligonucleotide consists of a locked nucleic acid (LNA) oligonucleotide.

8. The method of claim 7, wherein the oligonucleotide is selected from the group consisting of:
   (a) a nucleotide sequence comprising at least 16 contiguous nucleotides complementary to the sequence of SEQ ID NO: 1 and modifications excluding base substitutions thereof;
   (b) a nucleotide sequence comprising at least 16 contiguous nucleotides complementary to the sequence of SEQ ID NO. 2 and modifications excluding base substitutions thereof; and
   (c) a nucleotide sequence comprising at least 8 contiguous nucelotides complementary to the sequence of a fragment consisting of a subsequence of SEQ ID NO: 2 of at least 8 contiguous nucleotides thereof.

9. The method of claim 4, wherein the oligonucleotide is modified to include a 2'-deoxy-2'-fluoro-beta-D-arabinose backbone.

10. The method of claim 1, wherein the miRNA-762 inhibitor is associated with a carrier molecule selected from the group consisting of a nanoparticle, a liposome, and a lipoprotein.

11. The method of claim 1, wherein the subject does not have vascular calcification.

12. The method of claim 1, wherein the inhibitor is administered at a site of fibrosis, scarring, or keloid.

13. The method of claim 12, wherein the inhibitor is administered topically or by local injection.

14. The method of claim 1, wherein the inhibitor is associated with a device selected from the group consisting of a stent coated with the inhibitor and a bandage comprising the inhibitor.

15. A method of upregulating matrix degrading matrix metalloproteinases (MMPs) in a subject having fibrosis, scarring, or keloid, comprising:
   administering an effective amount a miRNA-762 inhibitor to the subject.

16. The method of claim 15, wherein the miRNA-762 inhibitor is administered at a site of fibrosis, scarring, or keloid.

17. A method of upregulating matrix degrading matrix metalloproteinases (MMPs) in a subject, comprising:
   administering an effective amount a miRNA-762 inhibitor to the subject;
   wherein the subject is identified as having or being at risk for developing perivascular fibrosis, fibrosis of a blood vessel, aortic stiffening/hypertension, vascular fibrosis, vascular disease, and vascular inflammation.

* * * * *

UNITED STATES PATENT AND TRADEMARK OFFICE
CERTIFICATE OF CORRECTION

PATENT NO. : 10,119,139 B2  
APPLICATION NO. : 15/265813  
DATED : November 6, 2018  
INVENTOR(S) : Harrison et al.

Page 1 of 1

It is certified that error appears in the above-identified patent and that said Letters Patent is hereby corrected as shown below:

In the Specification

Replace the second paragraph, which appears on Column 1, with the following:
Government Support
This invention was made with government support under grant numbers HL039006, HL105294, and HL058000 awarded by the National Institutes of Health. The government has certain rights in the invention.

Signed and Sealed this
Tenth Day of December, 2019

Andrei Iancu
*Director of the United States Patent and Trademark Office*